United States Patent [19]
Berman

[11] 3,930,507
[45] Jan. 6, 1976

[54] ADJUSTABLE ORAL AIRWAY

[76] Inventor: Robert A. Berman, 501 Cedar Hill Road, Far Rockaway, N.Y. 11691

[22] Filed: Feb. 18, 1975

[21] Appl. No.: 550,201

[52] U.S. Cl. .............................. 128/345; 128/351
[51] Int. Cl.² ................. A61M 29/00; A61M 16/00
[58] Field of Search ............. 128/208, 341, 345, 351

[56] References Cited
UNITED STATES PATENTS

| 2,127,215 | 8/1938 | Gwathmey | 128/208 |
| 2,599,521 | 6/1952 | Berman | 128/341 X |
| 3,057,347 | 10/1962 | Mc Gee | 128/351 X |
| 3,419,004 | 12/1968 | Berman | 128/351 X |
| 3,543,751 | 12/1970 | Sheffer | 128/208 |

*Primary Examiner*—Channing L. Pace
*Attorney, Agent, or Firm*—Stoll and Stoll

[57] ABSTRACT

An adjustable oral airway comprising a superior section and inferior section joined at their inner ends by a hinge member, and slidably secured relative to each other at the mouthpiece end, as by a tongue and groove slidable joint. The superior and inferior sections may be spaced a greater or a lesser distance from each other by means of sliding the upper and lower sections of the mouthpiece to improve ease of insertion and removal and to expand or reduce the pharynx, lifting the epiglottis and improving the breathing ability of an unconscious patient.

4 Claims, 12 Drawing Figures

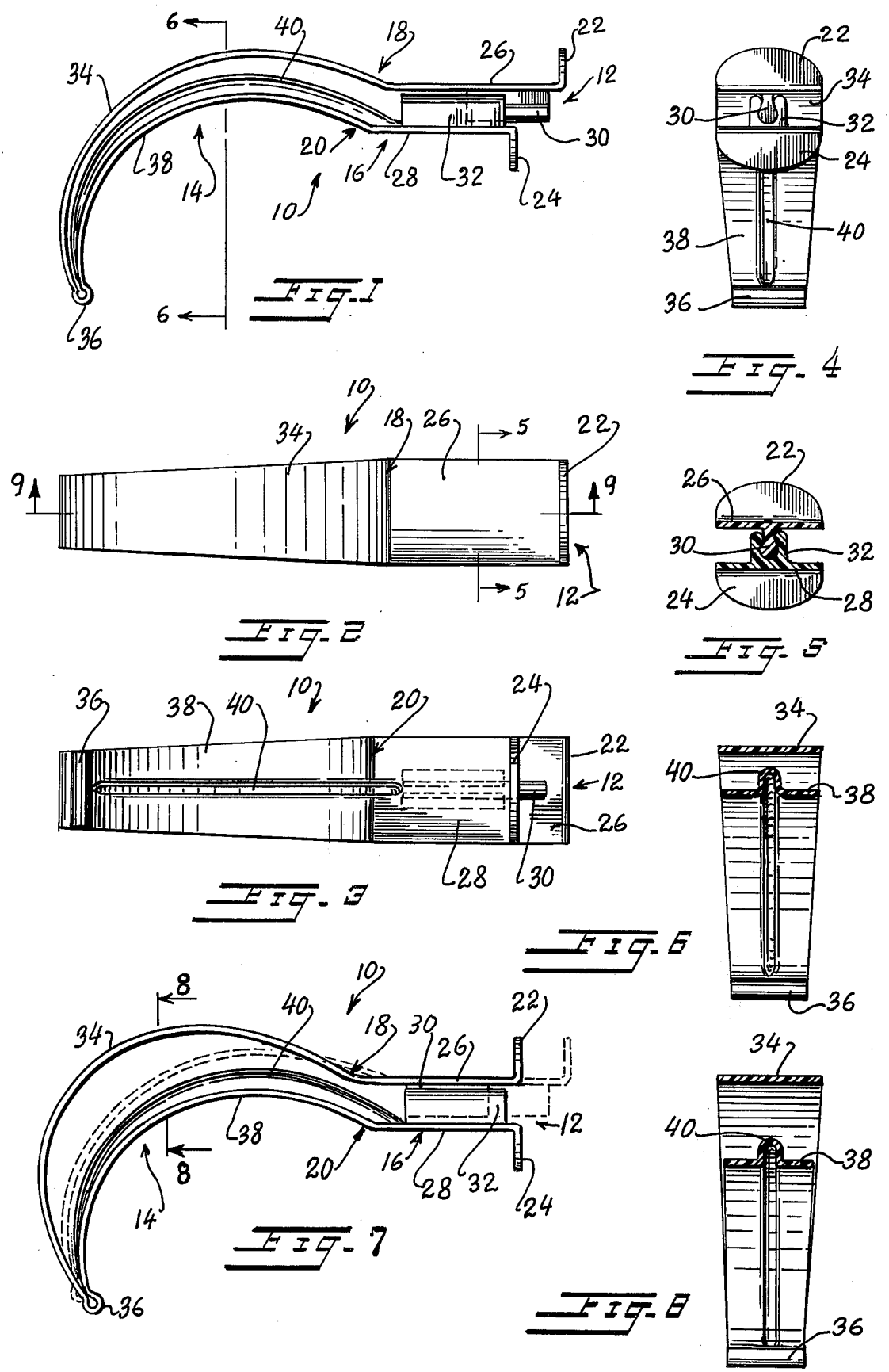

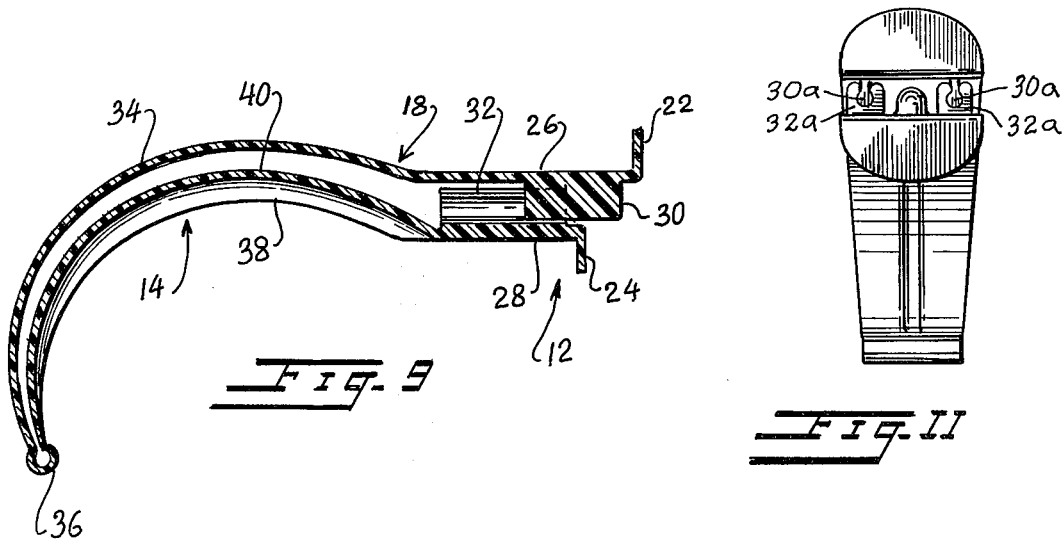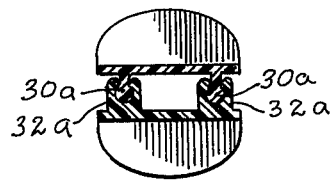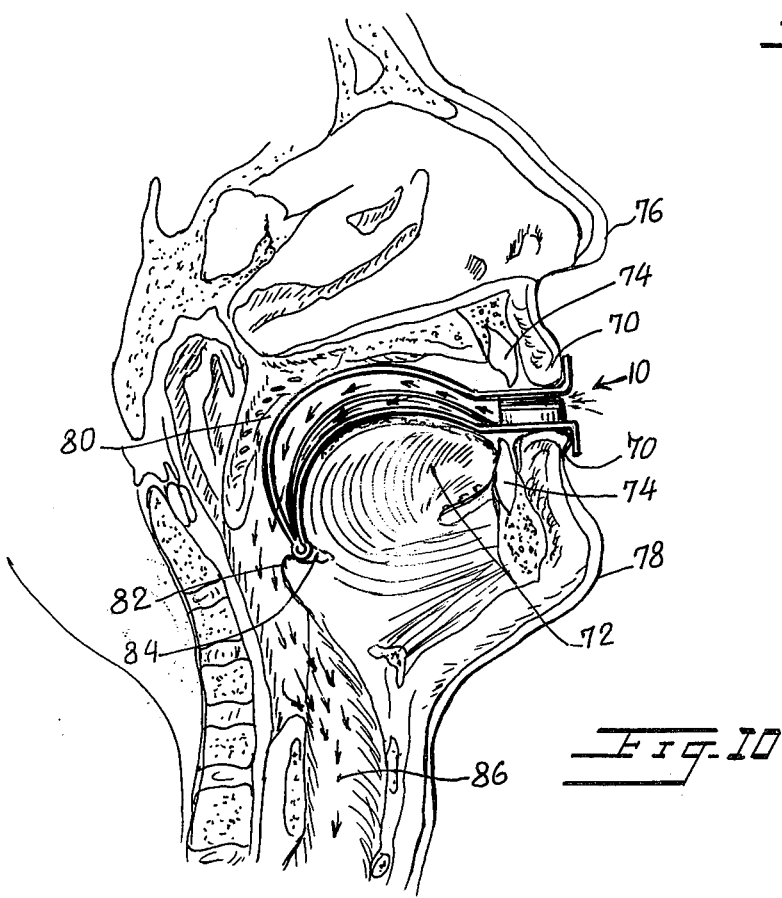

3,930,507

ADJUSTABLE ORAL AIRWAY

BACKGROUND OF THE INVENTION

It is now well-known to utilize an airway for the purpose of aiding the breathing of unconscious patients. Reference may be had to U.S. Pat. No. 2,599,521, which issued June 3, 1952 to the present inventor, for a description of a conventional airway now known in medical practice as the Berman Oral Airway. The Berman Oral Airway, and later devices modelled after it, is employed in the practice of surgery and medicine by insertion in the mouth and pharynx of a patient to provide a channel for respiratory purposes, particularly in unconscious patients. It is the purpose of the airway to prevent respiratory difficulty by preventing collapse of the pharynx walls or obstruction of the pharynx by the tongue.

The Berman Oral Airway and later such devices are available to the medical profession in a number of different sizes for use in infants, small children, children, medium adults and large adults. However, each size constitutes a unitary member which may not itself be adjusted in size, shape, or contour. Thus, conventional airways are substantially rigid structures which may not be altered in use to fit particular patients, particular problems or particular changes in patient condition or position.

SUMMARY OF THE INVENTION

Accordingly, the present invention provides an oral airway which is flexible, adjustable in contour, and which is adapted for use in a wide variety of situations, including situations which may change.

The present invention provides an airway which may be made smaller in cross-sectional area for case of insertion and removal and which may be made larger in cross-sectional area when in position.

The present invention provides an oral airway which adjusts the cross-sectional area of the pharynx so as to provide the maximum air flow possible consistent with a patient's anatomy. Moreover, the present invention provides an oral airway which may be adjusted during use to improve breathing characteristics, to improve access for removal of foreign matter such as mucous, and to prevent the build up of such foreign matter.

Briefly, but not by way of limitation, the present invention provides an adjustable oral airway having a superior section and an inferior section. Each section is provided with a curved flexible leaf member joined at the inner end by a hinge member. Each section is provided with a mouthpiece end, and a sliding joint section is provided between the leaf sections and the mouthpiece sections of the superior and inferior members. The sliding section may be a tongue and groove. The inferior leaf is provided with a longitudinal rib which improves rigidity of the lower leaf and provides improved air flow characteristics.

BRIEF DESCRIPTION OF THE DRAWING

FIG. 1 is a side view of the adjustable oral airway of the present invention, showing the superior section in the withdrawn position, thereby reducing the cross-sectional size of the leaf section of the airway for ease of insertion and removal.

FIG. 2 is a top view of the adjustable oral airway shown in FIG. 1.

FIG. 3 is a bottom view of the adjustable oral airway shown in FIG. 1.

FIG. 4 is a front view of the adjustable oral airway shown in FIG. 1.

FIG. 5 is a cross-sectional view taken across line 5—5 of FIG. 2, showing the opposite side of the mouthpiece shown in FIG. 4.

FIG. 6 is a cross-sectional view taken across line 6—6 of FIG. 1.

FIG. 7 is a view similar to that of FIG. 1 but showing the upper mouthpiece slid to its inward position. The original position as shown in FIG. 1 is noted in FIG. 7 in phantom. The slight downward and rightward movement of the inner end and hinge of the adjustable oral airway is slightly exaggerated for clarity.

FIG. 8 is a cross-sectional view taken across line 8—8 of FIG. 7. In comparison with FIG. 6, this figure shows the cross-sectional expansion of the airway upon inward sliding of the superior section.

FIG. 9 is a cross-sectional view taken across line 9—9 of FIG. 2.

FIG. 10 is a sagittal section through the mouth, tongue, larynx, pharynx and nasal cavity of a patient showing the adjustable oral airway of the present invention inserted in the mouth and pharynx with the inner end located in the valeqular. The superior member has been slid to its innermost position.

FIG. 11 is a view similar to that of FIG. 5 but showing a modified embodiment wherein there are a pair of parallel tongue and groove sliding members.

FIG. 12 is a view similar to that of FIG. 4 but showing the embodiment of FIG. 11.

DESCRIPTION OF PREFERRED EMBODIMENTS OF THE INVENTION

With reference to the drawing, the adjustable oral airway 10 of the present invention comprises a mouthpiece section 12 at one end, a leaf section 14 at the opposite end, and a slide section 16 between mouthpiece section 12 and leaf section 14. Adjustable oral airway 10 comprises a superior member 18 and an inferior member 20, superior member 18 lying above inferior member 20 when in the position shown in FIG. 1. This is the position of use for an upright patient such as is shown in FIG. 10. All directions hereinafter discussed in the description and referred to in the appended claims are with reference to the FIG. 1 orientation of adjustable oral airway 10. In addition, inward as used in the description and in the appended claims refers to a direction inwardly of the mouth and pharynx of the patient, being to the left in the FIG. 1–FIG. 10 orientation. Outward would be in the reverse direction, that is, to the right in the FIG. 1–FIG. 10 orientation.

The mouthpiece section 22 of superior section 18 comprises an upturned flange 22 and the mouthpiece section 24 of inferior section 20 comprises a downturned flange 24 corresponding generally in size and shape, although inverted, with upturned flange 22.

Slide section 16 of superior section 18 comprises a relatively planar upper base 26 and slide section 16 of inferior section 20 comprises a relatively planar lower base 28. Secured to upper base 26 is a tongue section 30 and secured to lower base 28 is a groove section 32 adapted to engage tongue 30 for linear motion with respect thereto. That linear motion is in a direction from mouthpiece section 12 toward leaf section 14 and back. When tongue 30 and groove 32 are engaged, upper base 26 and lower base 28 are substantially parallel. The tongue and groove members are between the upper base and the lower base.

Leaf section 14 of superior section 18 comprises a relatively flat curved band hereinafter referred to as upper leaf 34. Upper leaf 34 is arcuate, extending first above and then below the plane of upper base 26, in a direction inwardly of upper base 26. Upper leaf 34 terminates at inner end 36 of leaf section 14. Leaf section 14 of inferior section 20 comprises a substantially flat curved band, hereinafter referred to as lower leaf 38, with a longitudinally extending raised center rib 40. Lower leaf 38 is arcuate and follows substantially the same path as does upper leaf 34, first rising above and then falling below the plane of lower base 28 in a direction inwardly of adjustable oral airway 10. Lower leaf 38 is provided with a smaller radius of curvature than upper leaf 34, whereby lower leaf 38 curves more sharply beneath upper leaf 34. From a spaced distance apart at the juncture of upper leaf 34 to upper base 26 and the juncture between lower leaf 38 and lower base 28, the upper and lower leaves maintain a spaced relationship until reaching inner end 36, whereat both leaves are connected. Inner end 36 comprises a hinge.

Use and operation of the adjustable oral airway 10 of the present invention is now clear. With airway 10 in the position shown in FIG. 1, that is, with superior section 18 withdrawn, being drawn outwardly of the patient, to the right as shown in FIG. 1, and to the right with respect to inferior section 20, the distance between upper leaf 34 and lower leaf 38 as shown in FIG. 6 is at a minimum. Airway 10 may be inserted into the patient's mouth and pharynx with inner end 36 resting against the epiglottis. In this position, airway 10 acts much like a conventional airway in that it restrains collapse of the pharynx and restrains the tongue against sliding rearwardly to close off the pharynx.

Superior section 18 is now slid inwardly a desired amount, that is toward the patient's mouth in a direction to the left of FIG. 1 and to the left with respect to inferior section 20. by virtue of the linear motion controlled by tongue 30 and groove 32 at slide section 16, by virtue of inner end 36 and the hinging action provided between upper leaf 34 and lower leaf 38, and by virtue of the flexibility of upper leaf 34, the distance between upper leaf 34 and lower leaf 38 is increased as may be seen in FIGS. 7 and 8. The increase in distance between upper leaf 34 and lower leaf 38 corresponds to an increase in the cross-sectional area of leaf section 14 which accordingly provides an increased cross-sectional area of the patient's pharynx yielding markably superior air-flow characteristics and breathing capability for the patient. Moreover, there is less chance of a mucous build-up blocking off the pharynx, there is a greater opportunity to insert surgical applicances, and the size of the pharynx may be controlled within the limits of the sliding ability of superior section 18 relative to inferior section 20. Moreover, the increased cross-sectional area of airway 10 occurs at leaf section 14, in the pharynx, and not at slide section 16, in the mouth and accordingly, there is less chance for airway 10 to become dislodged while in use. Of course, intentional removal of airway 10 is easily accomplished by sliding superior section 18 outwardly, that is, out of the patient's mouth to the right as shown in FIG. 1 and to the right with respect to inferior section 20, thereby reducing the distance between upper leaf 34 and lower leaf 38, reducing the cross-sectional area of leaf section 14, and making removal easily accomplished.

It is, of course, entirely possible to have more than one tongue and groove slide member, as shown in FIGS. 11 and 12. In the embodiment shown in FIGS. 11 and 12 there are a pair of parallel tongue and groove members 30a and 32a, respectively. Such a pair of tongue and groove members prevents twisting of the mouthpiece in the event the patient is bitting hard.

Further modification may, of course, be had within the scope of the invention. For example, raised rib 40 in lower leaf 38 imparts rigidity to that leaf as compared with the more flexible upper leaf 34. Moreover, rib 40, being an open channel on its bottom edge as may be seen in FIG. 6, provides an additional air-flow cavity which aids in patient breathing. Reduction in the size of the raised rib, or the placement of an additional rib on upper leaf 34, will alter the relative flexibility characteristics of each leaf such that longitudinal sliding of slide section 16 will result in different expansion characteristics of leaf section 14.

Adjustable oral airway 10 may be made from any suitably strong, relatively soft resilient material such as polyethylene.

For ease of understanding FIG. 10, the following reference numerals have been applied: lips 70, tongue 72, teeth 74, nose 76, chin 78, pharynx 80, epiglottis 82, vallecular 84 and trachea 86.

What is claimed is:
1. An adjustable oral airway comprising:
   a. a narrow, elongated superior section and a narrow, elongated inferior section, said superior and inferior sections being attached to each other at one end and being adapted for relative linear motion at their opposite end,
   b. said superior section and said inferior section each being provided with a mouthpiece section, a leaf section, and a sliding section between said mouthpiece section and said leaf section.
2. An adjustable oral airway in accordance with claim 1, wherein;
   a. said leaf section of said superior section is arcuate,
   b. said leaf section of said inferior section is arcuate, the radius of curvature of said inferior section leaf section being less than the radius of curvature of said leaf section of said superior section,
   c. said leaf sections being connected at said one end by means of a hinge.
3. An adjustable oral airway in connection with claim 2, wherein:
   a. said slide section comprises at least one tongue and groove slide,
   b. whereby said superior section may slide linearly with respect to said inferior section.
4. An adjustable oral airway in accordance with claim 3, wherein:
   a. said leaf section of said inferior section has a raised rib between its ends,
   b. whereby said leaf section of said inferior section is less flexible than said leaf section of said superior section.

* * * * *